(12) United States Patent
Nimri

(10) Patent No.: US 9,040,309 B2
(45) Date of Patent: May 26, 2015

(54) BINDING LAYER AND METHOD FOR ITS PREPARATION AND USES THEREOF

(75) Inventor: Shai Nimri, Kibbutz Nir David (IL)

(73) Assignee: BIO-RAD HAIFA LTD., Haifa (IL)

( * ) Notice: Subject to any disclaimer, the term of this patent is extended or adjusted under 35 U.S.C. 154(b) by 518 days.

(21) Appl. No.: 11/471,716

(22) Filed: Jun. 21, 2006

(65) Prior Publication Data

US 2007/0117199 A1    May 24, 2007

Related U.S. Application Data

(60) Provisional application No. 60/730,375, filed on Oct. 27, 2005.

(51) Int. Cl.
G01N 33/548 (2006.01)
G01N 33/543 (2006.01)

(52) U.S. Cl.
CPC ........ *G01N 33/54353* (2013.01); *G01N 33/548* (2013.01)

(58) Field of Classification Search
CPC ............... G08L 1/00; G08L 3/00; G08L 5/00; G08L 5/08; G08L 5/10; A61L 24/08; A61K 31/721; A61K 31/722; A61K 31/728; A61K 31/716; A61K 31/726; G01N 33/548; G01N 33/54653; G01N 33/53; G01N 33/54306; C08B 37/003; C08B 37/0072; C08B 37/0075
USPC .......... 435/135, 136; 436/525, 527, 528, 529, 436/530, 532, 80, 823; 530/402, 403, 406
See application file for complete search history.

(56) References Cited

U.S. PATENT DOCUMENTS

| 3,847,889 A | 11/1974 | Fryklund et al. |
| 3,873,514 A | 3/1975 | Chu et al. |
| 5,242,828 A | 9/1993 | Bergström et al. |
| 5,436,161 A | 7/1995 | Bergström et al. |
| 5,561,069 A * | 10/1996 | Brigham-Burke et al. ... 436/518 |
| 7,202,358 B2 * | 4/2007 | Hargreaves .................. 536/25.3 |
| 2004/0018498 A1 | 1/2004 | Hargreaves |

FOREIGN PATENT DOCUMENTS

| EP | 1 343 010 | 9/2003 |
| GB | 2 278 447 A | 11/1994 |
| JP | 8-507602 A | 8/1996 |

(Continued)

OTHER PUBLICATIONS

Lofas S. Dextran modified self-assembled monolayer surfaces for use in biointeraction analysis with surface plasmon resonance. Pure and Appl. Chem. 1995, vol. 67, No. 5, pp. 829-834.*

(Continued)

*Primary Examiner* — Shafiqul Haq
(74) *Attorney, Agent, or Firm* — Vorys, Sater, Seymour and Pease LLP; Susanne M. Hopkins; Ari G. Zytcer

(57) ABSTRACT

The invention provides a binding layer comprising a polysaccharide substituted by carboxylic groups or derivatives thereof exhibiting high performance in the binding of ligand molecules and in the interaction thereof with analyte molecules. A method for the preparation of the binding layer and for the assaying of various analyte molecules is also provided.

16 Claims, 7 Drawing Sheets

(56) References Cited

FOREIGN PATENT DOCUMENTS

| JP | 2002-522790 A | 7/2002 |
|---|---|---|
| JP | 2004-359895 A | 12/2004 |
| WO | 92/21976 | 12/1992 |
| WO | 94/19694 A1 | 9/1994 |
| WO | 99/55715 A2 | 11/1999 |
| WO | 02/092834 A2 | 11/2002 |

OTHER PUBLICATIONS

Hattori et al. Functional changes of b-lactoglobulin by conjugation with carboxymethyl dextran. J. Agric. Food Chem. 1994, vol. 42, pp. 2120-2125.*

Löfås et al., "A Novel Hydrogel Matrix on Gold Surfaces in Surface Plasmon Resonance Sensors for Fast and Efficient Covalent Immobilization of Ligands". *J. Chem Soc., Chem. Commun.*, pp. 1526-1528, 1990.

Johnsson et al., "Immobilization of Proteins to a Carboxymethyldextran-Modified Gold Surface for Biospecific Interaction Analysis in Surface Plasmon Resonance Sensors". *Analytical Biochemistry*, vol. 198, pp. 268-277, 1991.

Löfås et al., "Methods for Site Controlled Coupling to Carboxymethyldextran Surfaces in Surface Plasmon Resonance Sensors". *Biosensors & Bioelectronics*, vol. 10, pp. 813-722, 1995.

Stolowitz, M.L., et al., "Phenylboronic Acid-Salicylhydroxamic Acid Bioconjugates. 1. A Novel Boronic Acid Complex for Protein Immobilization", *Bioconjugate Chem*, vol. 12, pp. 229-239, (2001).

Bombardieri, G., et al., "Studies on Dextran and Dextran Derivatives, XIV. Metal Binding Properties of Succinyl- and Phthalyl-Dextrans", *Archives of Biochemistry and Biophysics*, vol. 127, pp. 766-769, (1968).

Wiley, J.P., et al., "Phenylboronic Acid-Salicylhydroxamic Acid Bioconjugates. 2. Polyvalent Immobilization of Protein Ligands for Affinity Chromatography", *Biconjugate Chem.*, vol. 12, pp. 240-250, (2001).

Wei, X., et al., "Integration of Enzymes and Electrodes: Spectroscopic and Electrochemical Studies of Chitosan-Enzyme Films", *Anal. Chem.*, vol. 74, pp. 5039-5046, (2002).

Zhang, J., et al., "A New Method for the Synthesis of Selenium Nanoparticles and the Application to Construction of $H_2O_2$ Biosensor", *Chinese Chemical Letters*, vol. 15, No. 11, pp. 1345-1348, (2004).

Deckert, A.A., et al., "Comprehensive Study of the Formation and Reaction of a Tethered N-Hydroxysulfosuccinimidyl Ester Used to Covalently Tether Proteins to Surfaces", *J. Phys. Chem. B*, vol. 108, pp. 15808-15814, (2004).

Löfås, S., "Dextran modified self-assembled monolayer surfaces for use in biointeraction analysis with surface plasmon resonance", Pure & Appl. Chem., vol. 67, No. 5, pp. 829-834, (1995).

* cited by examiner

Poly(acrylic acid)

Poly(methacrylic acid)

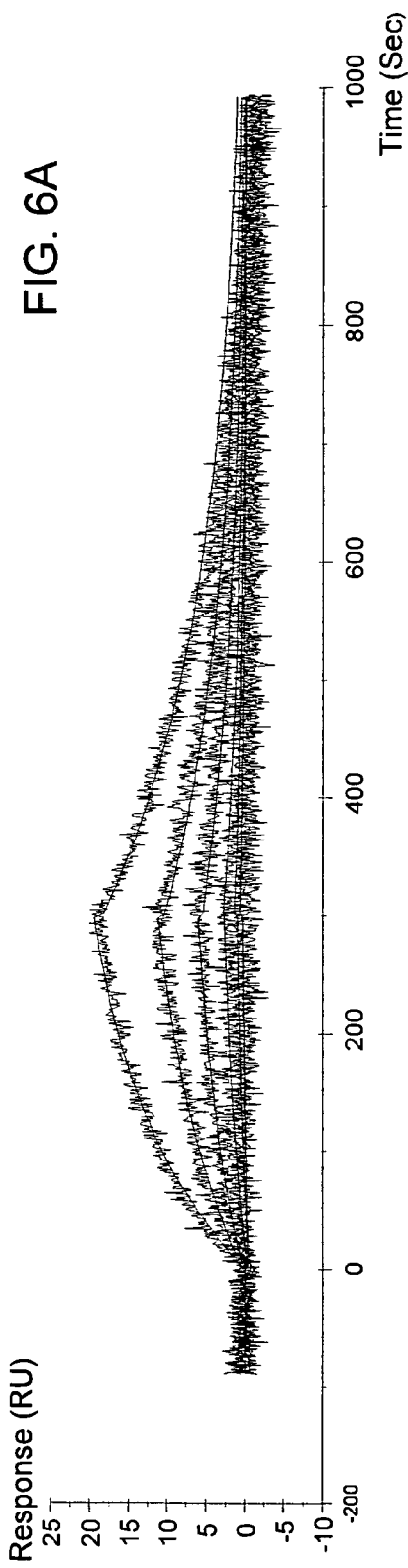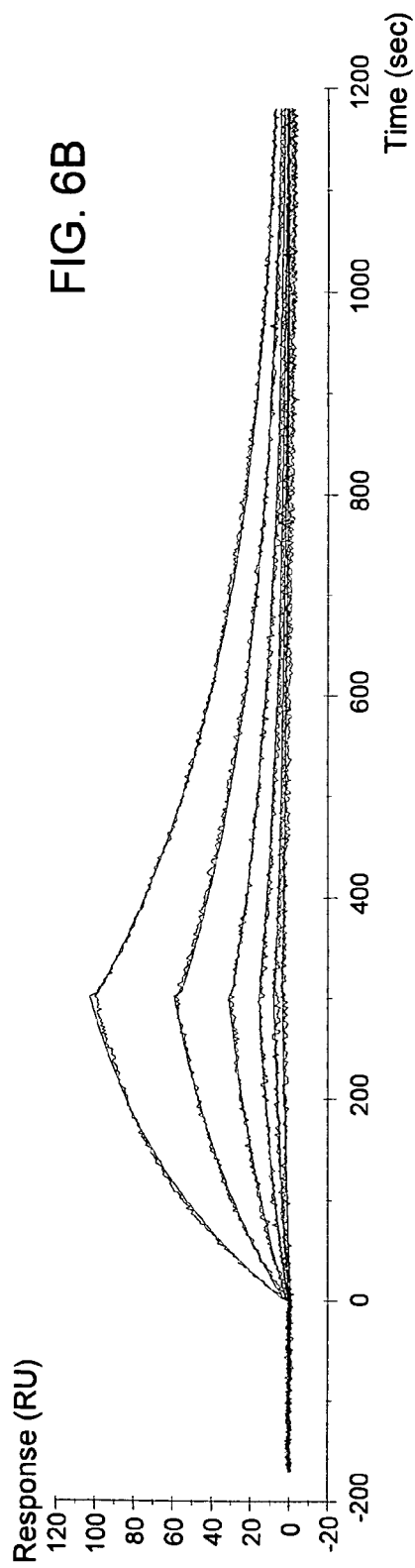

BINDING LAYER AND METHOD FOR ITS PREPARATION AND USES THEREOF

This application claims the benefit of prior U.S. provisional patent application No. 60/730,375 filed Oct. 27, 2005, the contents of which are hereby incorporated by reference in their entirety.

FIELD OF THE INVENTION

The present invention generally concerns binding layers and matrices for use in bioassays and biosensors.

BACKGROUND OF THE INVENTION

Biosensors have been developed to detect a variety of biomolecular complexes including oligonucleotides, antibody-antigen interactions, hormone-receptor interactions, and enzyme-substrate interactions. In general, biosensors consist of two components: a highly specific recognition element and a transducer that converts the molecular recognition event into a quantifiable signal. Such signal transduction may be accomplished by many methods, including fluorescence, interferometry, and gravimetry.

Direct methods that do not require labeling of analytes with fluorescent compounds are of interest due to the relative assay simplicity and ability to study the interaction of small molecules and proteins that are not readily labeled. Direct optical methods include surface plasmon resonance (SPR), grating couplers, ellipsometry, evanescent wave devices, and reflectometry. Theoretically predicted detection limits of these detection methods have been determined and experimentally confirmed to be feasible down to diagnostically relevant concentration ranges.

Typically in real-time studies of biomolecular complexes or interactions, immobilized ligand molecules attached to the surface of a sensor-chip e.g. through a chemical binding layer are brought into contact with analyte molecules. Thereupon interaction ensues which may be monitored by one or more of the aforementioned methods of detection. As the efficacy of such studies may depend primarily on the ligand molecules, efficient immobilization of ligand molecules is often a basic and most crucial requirement. High density of ligand molecules increases the amount of analyte molecules that interact therewith and thus afford a more sensitive measurement with a lower limit of detection.

In addition to the amount of immobilized ligand, another critical aspect is the maintenance of the biological activity of the ligand upon its attachment to the surface. Conservation of high ligand activity guarantees that large number of analyte molecules would interact with the ligand, yielding a more sensitive assay. The ligand activity is strongly dependant on the biocompatibility of the binding layer, as well as on various parameters of the immobilization method and process.

Improved assay sensitivity is necessary especially in the study of interactions between macromolecules such as proteins and small molecules, whereas a result of the differences in size between the protein ligand and the small analyte molecule, the resulting signal may be relatively low. Such bioassays are of special importance in the area of drug discovery, in which measuring the binding of small target molecules to large protein-based receptors is often sought.

One of the most accepted methods for attachment of ligand molecules to a surface is based on using binding layers that contain carboxylic groups (CGs), present in the acid form and/or as a corresponding carboxylate salt. The CGs are commonly activated to form reactive esters that then react with nucleophilic groups of the ligand molecules, mainly with primary amine groups to form covalent amide bonds. The most commonly used activation solutions consists of a mixture of a water-soluble carbodiimide, most often N-ethyl-N'-(3-dimethylaminopropyl) carbodiimide (EDC), and N-hydroxysuccinimide (NHS), to form reactive NHS esters. European Patent No. 1343010 teaches an alternative, less common procedure, in which N-hydroxysulfosuccinimide (sulfo-NHS) is used instead of NHS.

Among the various types of such binding layers, a frequently used layer in commercially-available biosensors is based on carboxymethyl dextran (CMD), as taught for example in Patents Nos. WO09221976 and U.S. Pat. No. 5,436,161, and demonstrated in scientific articles such as *J. Chem. Soc. Chem. Commun.* 1990, 1526-1528 and *Anal. Biochem.* 1991, 198, 268-277. It was reported that maximum 30-40% of the CGs in this layer can be activated to NHS esters using standard activation solutions. Additionally, it was shown that the CMD layer usually binds only part of the protein amount that was electrostatically adsorbed to it. In some cases, the binding was practically insufficient for performance of an interaction assay.

From another aspect, it was demonstrated that the activated layer has net negative electrostatic charge due to the presence of non-activated CGs. It is clear that this charge remains also after common deactivation step, in which the activated groups are reacted with ethanolamine to form neutral amides. The remaining charge is undesired at the interaction assay stage, since charged analyte molecules might interact non-specifically with the layer, causing possible interruptions and distortions in the assay results, as familiar to any person skilled in the art.

More efficient binding of ligand molecules can be obtained by direct coupling, or alternatively by using chemical or biological capturing moiety, such as biotin or avidin, antibodies, disulfide for thiol coupling, etc., as taught for example in *Biosensors Bioelec.* 1995, 10, 813-822. Layers amenable for more efficient activation are expected to be superior also when such moieties are used, due to higher amounts of bound capturing molecules.

Furthermore, the residual charge of such improved layers can be minimized more efficiently upon deactivation process, yielding more favorable environment for the interaction assay stage.

Thus, there exists the need for improved layers which are more amenable for activation, since they have potential to bind ligand molecules more efficiently and thus increase the assay sensitivity and lower the limit of detection.

SUMMARY OF THE INVENTION

According to the current invention, provided herein are improved binding layers, having significant benefits for use in bioassays and biosensors when compared with known and currently used matrices.

The innovative layers generally comprise a polysaccharide substituted by at least one carboxylic acid (an organic group —COOH) or derivative thereof, having an $\alpha$-atom bearing hydrogen atoms or carbon groups, namely each of the $\beta$-atoms to said CGs is a hydrogen or a carbon atom. Such CGs are herein referred to as "easily-activated carboxylic groups". These CGs are amenable for efficient activation upon exposure to standard activation solutions, e.g. which contain N-ethyl-N'-(3-dimethylaminopropyl) carbodiimide (EDC) and N-hydroxysuccinimide (NHS).

As it will be shown hereinbelow, at least 50% of the easily-activated CGs were activated for amine coupling under conditions which typically yield a maximum of 30-40% activation in the commonly used existing layers.

Consequently, these layers are capable of more efficient binding of ligand molecules. For example, the binding density of an antibody was doubled when CGs (as in prior-art layers) having an oxygen at the β-position (RO— group bound to the α-carbon), were transformed to easily-activated CGs.

More surprisingly, it was found that the improved layers can exhibit not only a more efficient ligand binding but also higher ligand activity, resulting in even more sensitive assays.

Furthermore, the electrostatic charge of the provided layers can be minimized efficiently upon subsequent processes of activation and deactivation. It will be demonstrated that a layer containing easily-activated CGs was neutralized using a process that showed almost no effect on similar layers containing the commonly used CGs, namely CGs which have oxygen groups substituted at their α-carbon.

Thus, in a first aspect of the invention, there is provided a binding layer comprising a polysaccharide substituted by at least one carboxylic group or derivative thereof, wherein each β-atom to said carboxylic group or derivative thereof is a hydrogen or a carbon atom, and wherein at least part of a plurality of said carboxylic groups or derivatives thereof are activated for binding of ligand molecules.

In one embodiment, the binding layer comprises a polysaccharide substituted by at least one carboxylic acid groups. In another embodiment, the binding layer comprises a polysaccharide substituted by at least one carboxylic acid derivative, as defined herein. In yet another embodiment, the binding layer comprises a polysaccharide which is substituted by a mixture of carboxylic acid groups and derivatives thereof. Such a mixture may be of any ratio; for example, at ratios of 1:1, 1:100; 1:1000, or vice versa, respectively, or any intermediate ratios.

In still another embodiment, the carboxylic groups or derivatives thereof, independently of each other, are bonded to the polysaccharide through linker molecules, having between 1 and 20 atoms, and which are chosen so as not to affect the structural, chemical or physical characteristics of the binding layer of the invention. Non-limiting examples of such linker molecules are linear carbon chain, oligo(ethylene glycol) chain or a peptide chain. Preferably, the linker is of two or three carbon atoms In another aspect of the present invention, there is provided a method for preparing a binding layer comprising at least one carboxylic group or a derivative thereof, each of said at least one carboxylic group or derivative thereof having at the β-atom a hydrogen or a carbon atom, said method comprising the steps of:
  providing a substrate having a surface;
  immobilizing a polysaccharide on the surface of said substrate;
  chemically modifying said polysaccharide to form a plurality of carboxylic groups to extend therefrom, wherein each β-atom to said carboxylic group is a hydrogen or a carbon atom; and
  activating at least part of said carboxylic groups for binding of ligand molecules, wherein said chemical modification step and said activation step, independently of each other, may occur either before, during or after said immobilization step. In one embodiment, the method further provides the step of deactivating said activated carboxylic groups.

In yet another aspect of the present invention, there is provided a method for assaying an interaction between ligand and analyte molecules, comprising the steps of: preparing a binding layer as detailed herein; binding to said layer at least one ligand molecule capable of interacting with at least one analyte molecule; reacting said ligand molecule with said analyte molecule to bring about an interaction between them; and assaying said interaction.

The term "binding layer" refers within the content of the present invention to a layer comprising a polysaccharide which is immobilized or coupled to a solid substrate, in such a way that the resulting coating is suitable for binding of molecules, through direct chemical substitution or through indirect modifications.

The term "substrate" refers typically to a solid substrate which may be any substrate having a surface suitable for use as a sensing element in bioassays or biosensors. It may be composed of various materials, such as glass, plastic, or free electron metal surfaces such as copper, silver, aluminum and gold; the sensor surface may also be lipophilic in nature, for example one which comprises alkyl chain having from 12 to 24 carbon atoms, such as stearylamine.

The term "sensing element" refers to any substrate that is sensitive, by itself or by combination with other means, to the presence, quantity, or chemical or physical state of an assayed analyte. Examples may be a prism, electrode, grating, etc.

The coating may be attached to the surface of the substrate by any immobilization method known to a person skilled in the art. As used herein, the term "immobilization" or any lingual variation thereof refers to affixation of one or more components of the coating via any chemical, physical or mechanical bonding force or process to the surface of the substrate. Preferably, the immobilization method produces covalent attachment.

The term "polysaccharide" refers to any polymer consisting of more than about 10 monosaccharide residues joined to each other by glycosidic linkages. Within the scope of the present invention, the term refers also to a plurality of monosaccharide or oligosaccharide units, not being linked to each other, bound to the surface of the solid substrate, thus forming a continuous layer of polysaccharide assembly. The polysaccharide or assembly thereof may consist of the same monosaccharide residues, or various monosaccharide residues or derivatives of monosaccharide residues.

Exemplary polysaccharides that may be useful in the present invention include dextran, heparan, heparin, hyaluronic acid, alginic acid, agarose, carageenan, pectin, amylopectin, amylose, glycogen, starch, cellulose, chitin, chitosan and various sulfated polysaccharides such as heparan sulfate, chondroitin sulfate, dextran sulfate, dermatan sulfate, or keratan sulfate.

The term "carboxylic group" or any lingual variation thereof refers to a carboxylic acid moiety (—COOH) or a corresponding carboxylate ion of any metal, e.g. sodium, potassium, magnesium etc., or non-metal, e.g. ammonium cation, etc. Optionally, the carboxylic group is attached to a linker of 1 to 20 atoms; preferably, the carboxylic group is attached to a linker of 2 to 3 carbon atoms.

The term "derivative of carboxylic group" or any lingual variation thereof refers to any functional group directly derived from a carboxylic group such as an ester, amide, anhydride, aldehyde or acyl halide, e.g. acyl chloride, acyl bromide. Preferably, the derivatives of the carboxylic groups are ester groups, more preferably NHS or sulfo-NHS ester, and even more preferably sulfo-NHS ester.

The native or chemically substituted CGs or derivatives thereof, extend from the polysaccharide outwards in a manner allowing further modification of these groups. The term "modification" or any lingual variation thereof refers within the scope of the present invention to any sort of alternation which would afford a change in the chemical structure of the polysaccharide or any group bonded thereto. The modification may be achieved by any method known to a person skilled in the art. Preferably, the modification results directly in a plurality of carboxylic groups which extend outwardly from the polysaccharide. However, such a result may also be achieved via two or more steps which would afford the final desired structure.

It should be noted that due to the size of the polysaccharide or the assembly thereof, some crowded or unavailable carboxylic acid groups may be present on the surface of the substrate after immobilization. The expression "carboxylic group which extend from the polysaccharide" or any lingual variation thereof, will therefore refer to CGs which are bonded to (i.e. substituted on) the polysaccharide and which are available for further modification. Such substitution may be chemical in nature and may be through covalent, ionic, or any other type of bonding. Preferably, the chemical substitution is covalent.

In one embodiment, the step of chemical modification includes a further chemical reaction of at least one carboxylic group or derivative thereof having β-oxygen atom. Such reaction may for example be the amidation of said groups or derivatives by β-alanine or any derivative thereof.

The term "plurality of carboxylic groups" refers to a population of said groups which are bonded to the polysaccharide, the size of said population being efficient of producing a measurable signal in the methods of analysis utilized for the assaying of the interaction between the ligand and analyte molecules. The term "at least part of a plurality . . . " refers to a part of said population being preferably at least between 10% and 100% activated, or being substantially fully activated. More preferably the population of carboxylic groups is at least 20% activated, 30% activated, 40% activated or most preferably at least 50% activated.

The term "activated for binding of ligand molecules" or any lingual variation thereof refers to the formation of moieties capable of binding ligand molecules upon direct chemical or biological reaction with them. The activated group may contain a leaving group, for example in the case of amine coupling with a reactive ester, anhydride or acyl halide. It may further contain a moiety that forms covalent bonds by various mechanisms, e.g. disulfide or maleimide moieties for binding of thiol groups, or amine moiety for coupling of aldehyde groups. The activated group may further contain a moiety that forms non-covalent interaction with the ligand, for example biotin moiety with avidin or vise versa; another example is a metal chelator for capturing recombinantly tagged proteins, e.g. nickel nitrilotriacetic acid (Ni-NTA) for capturing of histidine-tagged proteins. The moieties referred to herein are in the scope of the invention derivatives of said carboxylic groups.

The term "ligand molecule" refers to such molecules, biological or otherwise, capable of interacting with another molecule through a reversible or irreversible interaction, and which interaction may be assayed, namely identified, analyzed and quantified. Such ligand molecules are, for example, a nucleic acid, peptide, protein, polypeptide, antigen, polyclonal antibody, monoclonal antibody, single chain antibody, antibody fragment such as F(ab), F(ab')$_2$ and Fv fragments, glycan, small organic molecule, cell, virus, bacteria, or biological sample. The ligand molecule will typically be selected to specifically bind to said analyte partner that is added to the coated surface of the substrate. For example, where the ligand molecule is an antibody and its binding partner, i.e. analyte is a particular antigen, the antibody specifically binds to the particular antigen.

The term "analyte" or any lingual variation thereof refers within the scope of the present invention to the chemical undergoing analysis, i.e. presence, quantification or kinetics or thermodynamics of its interaction with ligand molecules is to be assayed. The analyte is typically the binding partner of the ligand bonded to the binding layer of the invention. The analyte to be assayed may for example be a nucleic acid, peptide, protein, polypeptide, antigen, polyclonal antibody, monoclonal antibody, single chain antibody, antibody fragment, glycan, small organic molecule, and others.

Preferably, such ligand-analyte interactions to be assayed are antibody-antigen interactions; protein-protein interactions, e.g. enzyme-inhibitor protein interactions; and protein-small molecule instructions.

The interaction between the two binding partners, namely the ligand and analyte may be assayed using any method known to a person skilled in the art. Such methods may be based on fluorescence, nuclear, magnetic, electrochemical or optical methods employed. Preferably, the methods employed are optical methods such as surface plasmon resonance (SPR).

The easily-activated CGs may be native to the polysaccharide or polysaccharide building blocks (monosaccharide, oligosaccharide) or may be substituted thereon by any chemical modification known to a person skilled in the art. For the transformation of various groups into carboxylic acid groups, see for example Comprehensive Organic Functional Group Transformation, Katritzky, Ed, 1995.

As stated hereinbefore, the benefits of the easily activated CGs arise from the substitution of hydrogen and/or carbon groups on the α-carbon. In other words, each of the β-atoms is a hydrogen or a carbon group. As known to a person versed in the art, the α-carbon is the carbon bearing the functional group moiety, in this case the carboxylic group moiety. The β-atoms are the atoms directly bonded to the α-carbon. Thus, in this case the CG may be a compound of the general structure $R_1R_2R_3C$—COOH wherein $R_1$ to $R_3$ are hydrogens or carbon groups. The α-carbon may be stereogenic, namely may be chiral and exist as one stereoisomer or the other, or as a mixture of both isomers (recimic or in excess), or may be extended from a cyclic or a macrocyclic backbone structure.

Within the scope of the present invention, the term "α-carbon" refers solely to the carbon atom at the alpha position to the terminus carboxylic groups which is used for the activation and eventual binding to the ligand molecule.

If the α-carbon is $sp^3$ hybridized, substitution may be by one hydrogen and two carbon groups, by two hydrogens and one carbon group or by three carbon groups. If the α-carbon is $sp^2$ hybridized, substitution may be by geminal hydrogen or a geminal carbon group and a double bond to a β-carbon at a cis- or trans- conformation. In case the α-carbon is sp hybridized, the α-carbon is triply substituted to a β-carbon. The carboxylic group may be threaded to the polysaccharide structure through the α-carbon or through any other atom.

As will be demonstrated herein binding layers based on polysaccharides having easily-activated CGs have significant benefits over the commonly-used matrices having CGs with electron withdrawing group such as RO— bound to the α-carbon.

BRIEF DESCRIPTION OF THE DRAWINGS

In order to understand the invention and to see how it may be carried out in practice, a preferred embodiment will now be described, by way of non-limiting examples only, with reference to the accompanying drawings, in which:

FIG. 2A—carboxymethyl dextran; FIG. 2B—alginic acid; FIG. 2C—carboxymethyl cellulose; FIG. 2D—pectin; FIG. 2E—Hyaluronic Acid.

FIG. 6 shows the two sensorgrams of the interaction between a mutant of the β-lactamase protein TEM1 to its inhibitor protein BLIP in six different concentrations. FIG. 6A shows the sensorgram for the reaction using NHS activation while FIG. 6B shows the sensorgram for the reaction using sulfo-NHS activation.

DETAILED DESCRIPTION OF THE INVENTION

The uniqueness of the invention disclosed herein lies in the development of SPR biosensors having binding layers that enable improved assay sensitivity, by gaining high densities of ligand while preserving its activity in an optimal way.

A limitation of the prior-art layers and method of activation was observed many times in the course of the investigation. When layers based on the common polysaccharide carboxymethyl dextran (CMD) were activated by a standard solution of EDC and NHS, frequently rather small part of the biomolecules that were adsorbed close to the surface was actually attached to the layer. Probably, the level of activation was insufficient for more efficient coupling. Similar observations were made in the case of other polysaccharides, such as alginic acid or carboxymethyl cellulose (see Examples 1 and 2).

Interestingly, synthetic polymers like poly(acrylic acid) or poly(methacrylic acid) exhibited much more efficient activation and subsequent immobilization. However, the ligand molecules exhibited low activity, probably due to lower biocompatibility of these polymers (see Examples 1-4).

Figure 1:
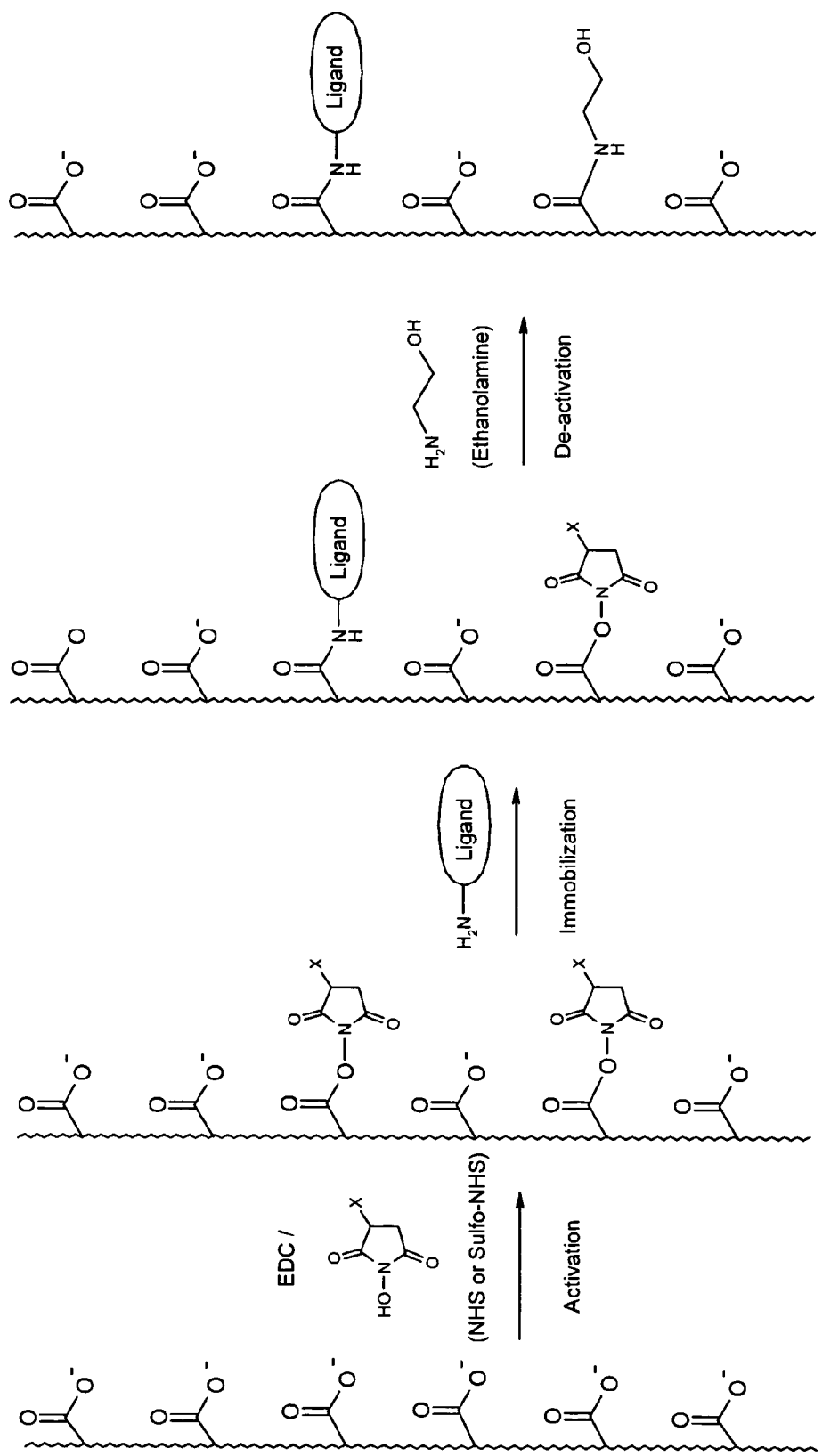
FIG. 1 is a schematic presentation of the prior-art procedures for immobilization of ligand molecules to carboxylic acid-containing binding layers, using activation by EDC/NHS (X=H) or sulfo-NHS (X=$SO_3^-$). The zigzag line represents the backbone of the binding layer and is not to mean that the carboxylic groups are directly bonded to the layer without any linking molecules.
Figure 2A:
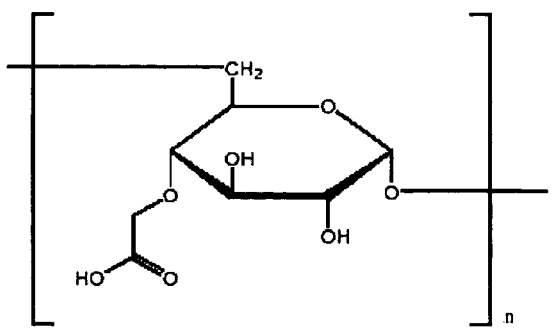
FIGS. 2A-2E demonstrate the structure of various carboxylic acid-containing polysaccharides.
Figure 2B:
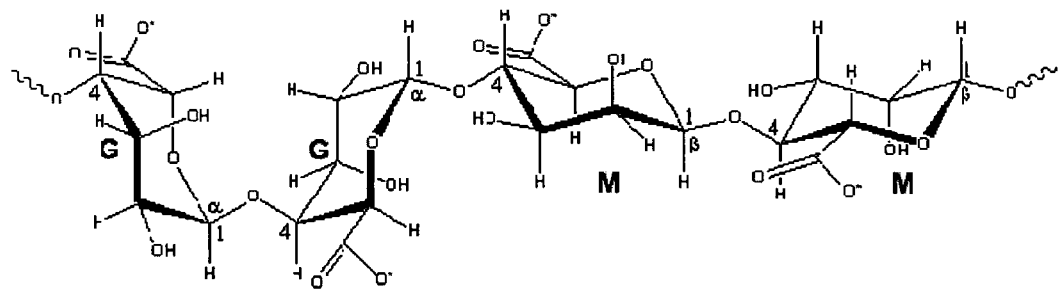
Figure 2C:
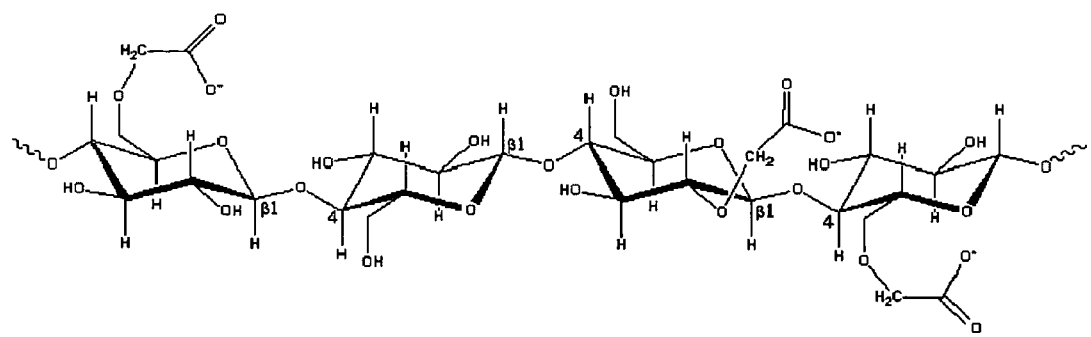
Figure 2D:
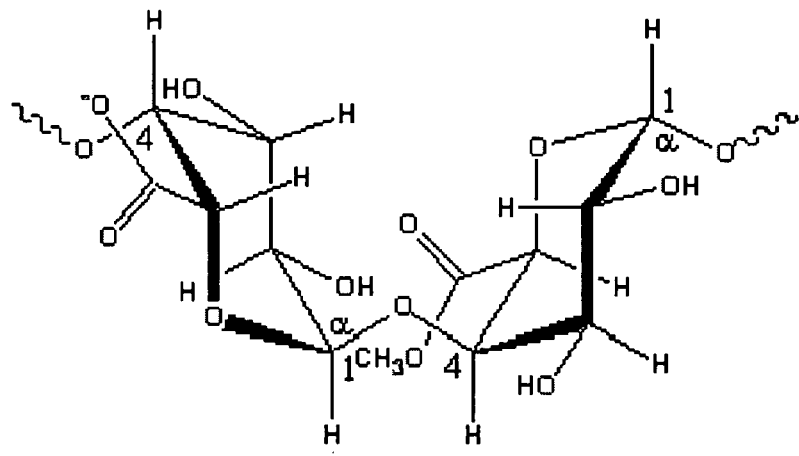
Figure 2E:
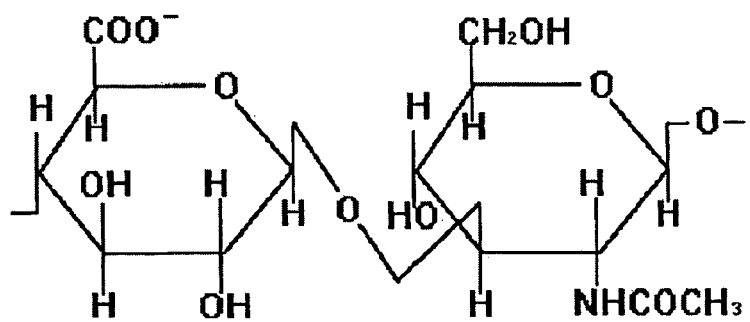
Figure 3A:
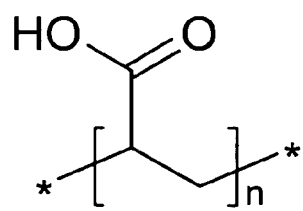
FIGS. 3A-3B show the general structure for two exemplary synthetic carboxylic acid-containing polymers, wherein n is an integer representing the number of repeating units.
Figure 3B:
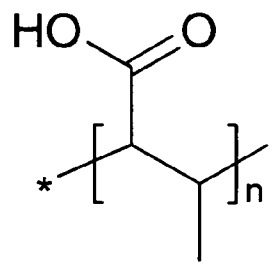

It has now been determined that the reduced activation of polysaccharides such as CMD, alginic acid and carboxymethyl cellulose and the other commercially available polysaccharides that contain CG moieties (e.g. hyalurunic acid and pectin) may stem from a common structural feature: an oxygen atom is located at a β-position to the CG (FIG. 2). In contrast, the synthetic polymers that exhibited higher activation have carbon or hydrogen atoms at the β-positions (FIG. 3) to the carboxylic acid moieties.

Therefore, the present invention provides binding layers with modified polysaccharides, which contain CGs having only carbon or hydrogen as β-atoms, namely at the β-position to the CG. As demonstrated herein bellow, such layers (Example 1, FIG. 4) exhibited both improved efficiency of immobilization and high ligand activity, leading to overall significant enhancement of the analyte signals (Examples 2-6).

Without wishing to be bound by theory, the observed differences may arise from a polar effect induced by the β-atoms on the CGs. Oxygen atoms, typically appearing in the polysaccharides as ether or hydroxyl groups, are involved in inductive electron withdrawal, while carbon atoms generally tend to release electrons. Consequently, β-carbon CGs are principally more electron rich (i.e. less acidic) than β-oxygen CGs. This electron enrichment may stabilize intermediates in the activation process, e.g. the O-acylisourea intermediate formed by the reaction of the CG with the carbodiimide, and therefore enhance the activation process and consequently the ligand immobilization. It should be further noted that when another electron withdrawing group, such as an amine group, was located at the β-position, e.g. by using binding layer based on carboxymethyl chitosan, the activation level of the CGs was similar to the level in β-oxygen CGs.

As known to a person versed in the art, the α-carbon is the carbon bearing the functional group moiety, in this case the carboxylic group. As stated hereinbefore, the layers of the invention comprise of carboxlic groups having at their β-positions either carbon groups or hydrogens. Such carbon groups may be selected from alkyl, cycloalkyl, heterocyclyl, aryl, heteroaryl, alkenyl, alkynyl, aralkyl, heteroaralkyl, carboxy, alkylaminocarbonyl, dialkylaminocarbonyl, arylalkylaminocarbonyl, arylaminocarbonyl, hydroxycarbonyl, alkoxycarbonyl, aryloxycarbonyl, alkylene, azaalkylene, thiaalkylene, alkenylene, alkynylene, cycloalkylene, arylene, heteroarylene, alkylidene, arylalkylidene, Cycloalkylidene, and amido. Each of said carbon groups, where possible, may be substituted or branched.

As used herein, alkyl, alkenyl and alkynyl carbon groups contain from 1 to 20 carbons, or 1 or 2 to 16 carbons, and are straight or branched. Alkenyl carbon groups of from 2 to 20 carbons contain 1 to 8 double bonds and alkenyl carbon chains of 2 to 16 carbons contain 1 to 5 double bonds. Alkynyl carbon chains of from 2 to 20 carbons contain 1 to 8 triple bonds, and the alkynyl carbon chains of 2 to 16 carbons contain 1 to 5 triple bonds. Exemplary alkyl, alkenyl and alkynyl groups herein include, but are not limited to, methyl, ethyl, propyl, isopropyl, isobutyl, n-butyl, sec-butyl, tert-butyl, isohexyl, allyl (propenyl) and propargyl (propynyl).

As used herein, each of the chemical terms used for the various radicals is meant in its broadest term. Specific definitions for each of said radicals may be found, for example, in "Chemical Terms" S. P. Parker, Ed., McGraw-Hill Book Co, New-York, 1985.

Figure 5:
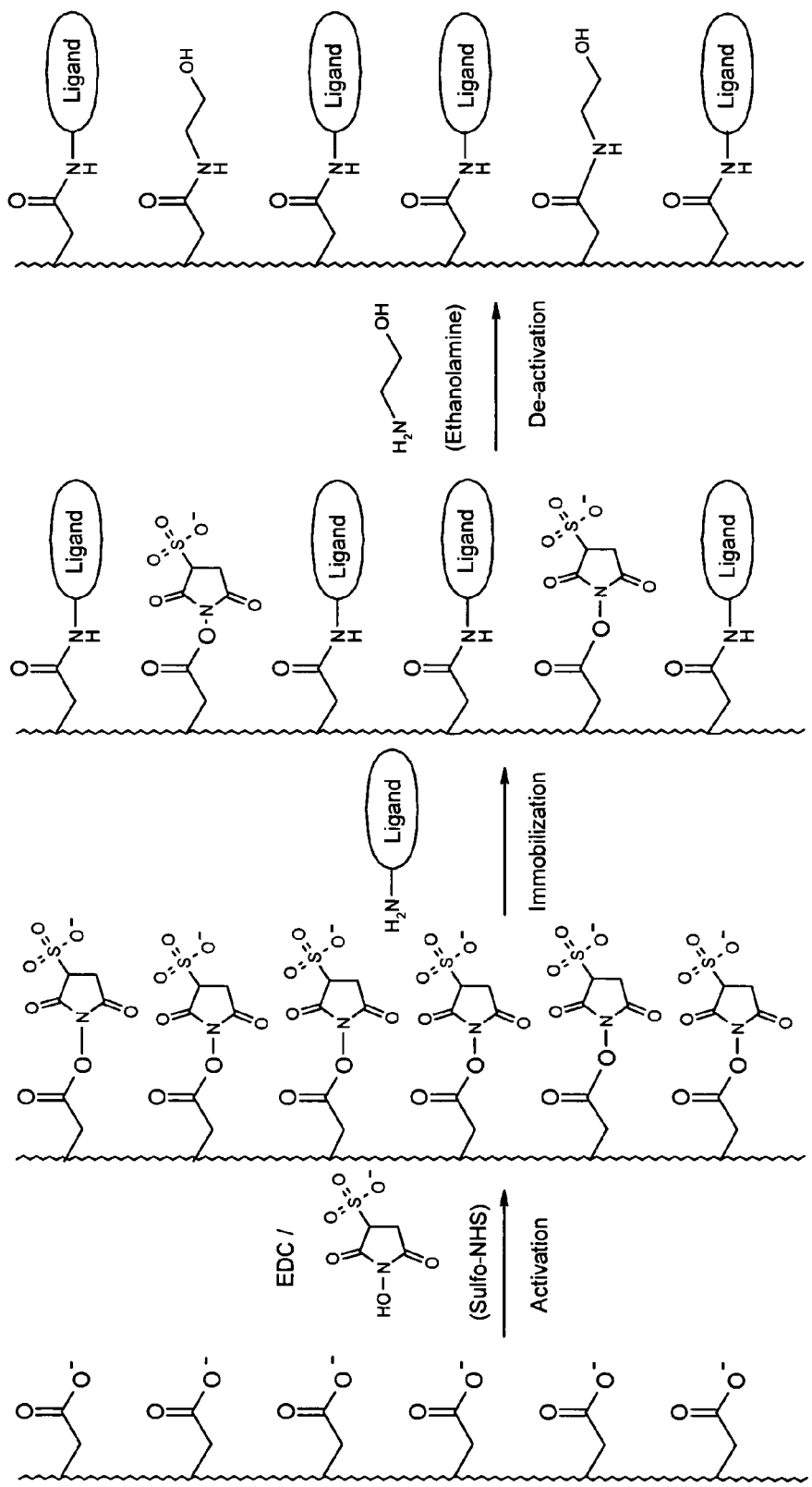
FIG. 5 is a schematic presentation of the efficient immobilization process according to the invention onto binding layers with easily-activated groups using EDC/sulfo-NHS activation. See the detailed description and FIG. 1 for schematic comparison to immobilization process onto prior-art binding layers.

NHS and sulfo-NHS were utilized in the activation process to form reactive esters. Still without wishing to be bound by theory, the uniqueness of the sulfo-NHS activated layer arises from its ability to maintain a great part of its negative charge upon activation. Consequently, the electrostatic pre-concentration to the activated layer is more efficient and high levels of immobilization are gained. This effect is much more prominent when layers with easily-activated CGs are used, since the degree of activation is higher than in the commonly-used layers (FIG. 5). The NHS or sulfo-NHS reagents may be incorporated to the layer upon on-line activation by the system operator (user), or be provided as intrinsic part of the layer (pre-activated layers).

It was found that high ligand density and activity, namely increased analyte signals, may be achieved in many biological models using the above approach (Examples 4-6). More specifically, it was observed that use of sulfo-NHS in the activation step may yield especially elevated analyte signals. The combination of polysaccharide-based binding layers with easily-activated CGs with sulfo-NHS activation leads to an optimal outcome in terms of ligand density and activity, thus representing a preferred embodiment of the invention.

In still another aspect of the invention, there are provided methods for minimizing the electrostatic charge of said layers after ligand immobilization. The high level of activation enables efficient charge minimization upon deactivation, using neutral (e.g. as in FIG. 5) or positive (e.g. as in FIG. 6) amine-containing molecules. The use of sulfo-NHS activation is preferred in this application also, in order to maintain the electrostatic charge of the layer during the immobilization step, before deactivation.

The following examples describe embodiments of the current invention in the formation of binding layers for SPR sensor chips and their use in biosensor applications, using a lab-prototype of the ProteOn XPR36 system (Bio-Rad). However, it should be stated that the present invention is intended for any application of binding layer or binding matrix known in the art. It can be implemented in any type of bioassay that requires immobilization of molecules to solid supports, for example ELISA. The principles of the invention may further be beneficial when used in purification methods that involve immobilization of molecules to microspheres, such as affinity chromatography.

Example 1

Preparation of Binding Layers

Thin layers of CMD, alginic acid, carboxymethyl cellulose or poly(acrylic acid) were attached to the gold surface of ProteOn SPR sensor chips, using a technology adopted from *Langmuir* 2001, 17, 8336-8340.

Briefly, each of the polymers was dissolved in aqueous solution and reacted with cystamine dihydrochloride in the presence of EDC and NHS, under conditions in which a few percent of the CGs of the polymer were modified with the cystamine dimer. Then, the cystamine disulfide bonds were reduced by tetra(carboxyethyl phosphine) and the solution was purified by dialysis. The product was an aqueous solution of the polymer, which now contained thiol end groups enabling its attachment to the gold surface.

The sensor chips were immersed in an aqueous solution containing the cystamine-modified polymers for 24 hours. The structure of the coating was varied by changing various parameters, such as the degree of cystamine modification, the concentration of the polymer, the solution pH and ionic strength. Consequently, after rinsing with water, various layers with different adsorption capacities of proteins were formed (Table 1).

Figure 4:
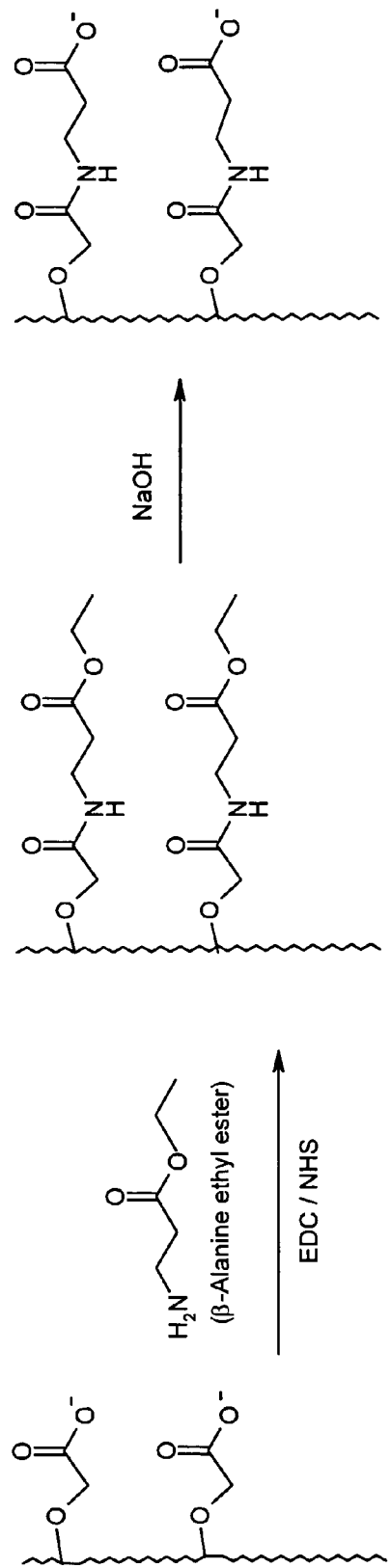
FIG. 4 depicts an exemplary method used to transform β-oxygen carboxylic acids to easily-activated β-carbon carboxylic acids according to the invention. The β-alanine ethyl ester used in this example is to be seen as one embodiment of the method.

Sensor chips of each type of polymer were used without further modification in various experiments, as detailed bellow. In addition, sensor chips that contained polysaccharides (CMD, alginic acid and carboxymethyl cellulose) were modified with β-alanine to contain easily-activated CGs (FIG. 4). These sensor chips were immersed for 16 hours in aqueous solution of 1 M β-alanine ethyl ester hydrochloride, 0.2 M EDC and 0.05 M NHS. The excess reagents were rinsed with water, and the ethyl ester protecting group was removed by hydrolysis upon immersion in 0.1 M NaOH for 1 hour. The produced binding layers were characterized and used for various experiments, as presented bellow.

Table 1 describes the binding layers that were used in the Examples brought herein. The adsorption capacities relate to a typical saturation value gained by electrostatic concentration of IgG-type antibody proteins to the surface.

The units of SPR signals used herein are response units (RU) as accepted in this field. One thousand RU is equivalent to a shift of 0.1 degree in the SPR curve, and known to represent a binding or adsorption of about 1 ng/mm$^2$ of protein to the surface.

TABLE 1

Various binding layers tested.

| Layer # | Polymer | Modification | Typical adsorption capacity of IgG proteins |
|---|---|---|---|
| 1 | Poly(acrylic acid) | None | 6,000 RU |
| 2 | Alginic acid | None | 6,000 RU |
| 2E | Alginic acid | β-Alanine | 6,000 RU |
| 3 | Carboxymethyl cellulose | None | 6,000 RU |
| 3E | Carboxymethyl cellulose | β-Alanine | 6,000 RU |
| 4 | Carboxymethyl dextran | None | 6,000 RU |
| 4E | Carboxymethyl dextran | β-Alanine | 6,000 RU |
| 5 | Alginic acid | None | 12,000 RU |
| 5E | Alginic acid | β-Alanine | 12,000 RU |

Example 2

Coupling Efficiency of a Representative Protein

Table 2 shows examples of ligand densities after adsorption or immobilization of Rabbit IgG antibody to five binding layers under similar conditions. The activation procedure included exposure to a solution of 0.2 M EDC and 0.05 M NHS or sulfo-NHS (7 min injection). The adsorption/immobilization of protein were done by exposure to a solution of 50 ug/ml Rabbit IgG in 10 mM sodium acetate buffer, pH 4.5 (6 min injection). Finally, the activated layers were deactivated by exposure to 1 M ethanolamine hydrochloride, pH 8.5 (5 min injection).

TABLE 2

Ligand densities after adsorption or immobilization of Rabbit IgG antibody.

| Layer # | Polymer | Modification | Adsorption capacity (no activation) | Binding after EDC/NHS activation | Binding after EDC/sulfo-NHS activation |
|---|---|---|---|---|---|
| 1 | Poly(acrylic acid) | None | 6,000 RU | 5,100 RU | 6,000 RU |
| 2 | Alginic acid | None | 6,100 RU | 3,000 RU | 3,100 RU |
| 3 | Carboxymethyl cellulose | None | 5,900 RU | 2,900 RU | 3,000 RU |
| 4 | Carboxymethyl dextran | None | 6,000 RU | 3,000 RU | 3,100 RU |
| 2E | Alginic acid | β-Alanine | 6,100 RU | 5,000 RU | 6,100 RU |
| 3E | Carboxymethyl cellulose | β-Alanine | 5,900 RU | 5,000 RU | 5,900 RU |
| 4E | Carboxymethyl dextran | β-Alanine | 6,000 RU | 5,100 RU | 6,000 RU |

Layer 1, based on poly(acrylic acid), showed relatively high levels of immobilization—close to its adsorption capacity after NHS activation, and equal to it after sulfo-NHS activation. The non-modified polysaccharide layers (2 to 4), on the other hand, exhibited lower immobilization values, and only minor difference between sulfo-NHS and NHS activation. Most importantly, modification of these layers with β-alanine (layers 2E to 4E, respectively) led to significantly increased binding, without affecting the adsorption capacity. The ligand densities were especially high after sulfo-NHS activation—the whole potential of adsorption capacity was fulfilled.

These results show that the modification of the polysaccharides to contain β-carbon CGs instead of β-oxygen CGs improved their ability to bind proteins after activation. The more prominent difference between NHS and sulfo-NHS indicates that the activation was more efficient after the modification with β-alanine, which formed the easily-activated CGs.

Example 3

Coupling Efficiency of Low-PI Protein

It is known that proteins with low isoelectric point (PI) are difficult to immobilize. Such proteins should be dissolved in a buffer with relatively low pH to render their positive charge and thus their electrostatic adsorption to the layer. Though, at low pH values, the negative charge of the CGs in the layer itself is decreased, and therefore the electrostatic attraction is weakened.

For example, it was reported that protein pepsin, which has a PI of 3.0, exhibited only negligible binding (70 RU) to CMD layer after standard EDC/NHS activation (*Anal. Biochem.* 1991, 198, 268-277). The results of a similar experiment using a binding layer based on alginic acid modified with β-alanine is shown in Table 2, layer 5E. These results show a much higher binding: 750 RU after EDC/NHS activation and 2050 RU upon EDC/sulfo-NHS activation. This advantage should be related to the use of easily-activated CGs, since the adsorption capacity of layer 5E was much lower than the reported CMD layer (12,000 RU IgG comparing to more than 30,000 RU IgG).

This experiment demonstrates that layers with easily-activated CGs can be used to perform assays with low-PI ligands which cannot be sufficiently immobilized to the commonly-used layers.

Example 4

Ligand Activity in Antibody-Antigen Interaction Study

Table 3 summarizes results of kinetic assays performed with various binding layers. Anti-interleukin-2 monoclonal antibody was immobilized after EDC/NHS activation, under conditions that were optimized for binding of about 2,000 RU of this protein. Then, the interleukin-2 analyte was flown over the surface in several concentrations from 2.5 to 80 nM. $R_{max}$ is the maximal analyte signal as calculated from the kinetic analysis. The ligand activity is defined as ($R_{max}$/Ligand Density)*(MW of ligand/MW of analyte).

TABLE 3

Results of kinetic assay between antibody and antigen performed with various binding layers.

| Layer # | Polymer | Modification | Ligand density | $R_{max}$ | Ligand activity |
|---|---|---|---|---|---|
| 1 | Poly(acrylic acid) | None | 2,000 RU | 60 RU | 30% |
| 2E | Alginic acid | β-Alanine | 2,000 RU | 195 RU | 98% |
| 3E | Carboxymethyl cellulose | β-Alanine | 2,100 RU | 200 RU | 95% |
| 4E | Carboxymethyl dextran | β-Alanine | 1,900 RU | 185 RU | 97% |

The results shown in Table 3 indicate that all polysaccharide-based layers, which were modified to contain easily-activated CGs, preserved high ligand activity of close to 100%. In contrast, the layer based on the synthetic poly(acrylic acid) caused significant decrease in the ligand activity. These differences can be related to the higher biocompatibility of the polysaccharides.

Example 5

Assay Sensitivity in Protein-Protein Interaction Study

Table 4 summarizes results of a kinetic assay between a mutant of β-lactamase protein (TEM1) and its inhibitor protein (BLIP). In all cases, binding layers based on alginic acid were used. The activation procedure included exposure to a solution of 0.2 M EDC and 0.05 M NHS or sulfo-NHS (7 min injection). The immobilization of ligand was done by exposure to a solution of 2 uM TEM1 in 10 mM acetate buffer, pH 4.0 (5 min injection). Finally, the activated layers were deactivated by exposure to 1 M ethanolamine hydrochloride, pH 8.5 (5 min injection). The BLIP analyte was injected in a series of concentrations, from 9 to 300 nM.

TABLE 4

Results of a kinetic assay between a mutant of β-lactamase protein (TEM1) and its inhibitor protein (BLIP).

| Layer # | Modification | Activation | Ligand Density | $R_{max}$ | Ligand Activity |
|---|---|---|---|---|---|
| 2 | None | EDC/NHS | 100 RU | <5 RU | NA |
| 2 | None | EDC/Sulfo-NHS | 100 RU | <5 RU | NA |
| 2E | β-Alanine | EDC/NHS | 600 RU | 20 RU | 20% |
| 2E | β-Alanine | EDC/Sulfo-NHS | 1,100 RU | 110 RU | 60% |

The non-modified layers were unable to bind sufficient amount of ligand, and thus the analyte signals were too low for kinetic analysis. After modification with β-alanine, the ligand binding was significantly improved and fine kinetic assay was recorded. The activation with sulfo-NHS instead of NHS not only increased the ligand amount but also its activity, resulting in a clearer sensorgrams with a higher signal to noise ratio (FIG. 6).

Hence, the modification with easily-activated CGs enabled carrying out an assay which would otherwise have been impossible to execute. The combination with sulfo-NHS activation was the most advantageous.

Example 6

Assay Sensitivity in Protein-Small Molecule Interaction Study

Table 5 summarizes results of a kinetic assay between the protein carbonic anhydrase II (CAII) and its inhibitor 4-carboxybenzenesulfonamide (CBS, molecular weight 201 g/mol). In all cases, binding layers based on alginic acid were used. The activation procedure included exposure to a solution of 0.2 M EDC and 0.05 M NHS or sulfo-NHS (7 min injection). The immobilization of ligand was done by exposure to a solution of 0.125 mg/ml CAII in 10 mM acetate buffer, pH 5.0 (9 min injection). Finally, the activated layers were deactivated by exposure to 1 M ethanolamine hydrochloride, pH 8.5 (5 min injection). The CBS analyte was injected in a series of concentrations, from 0.082 to 20 μmol/L.

TABLE 5

Results of a kinetic assay between the protein carbonic anhydrase II (CAII) and 4-carboxybenzenesulfonamide (CBS).

| Layer # | Modification | Activation | Ligand Density | $R_{max}$ | Ligand Activity |
|---|---|---|---|---|---|
| 5 | None | EDC/NHS | 2,800 RU | 9 RU | 55% |
| 5 | None | EDC/Sulfo-NHS | 2,900 RU | 10 RU | 58% |
| 5E | β-Alanine | EDC/NHS | 5,100 RU | 26 RU | 76% |
| 5E | β-Alanine | EDC/Sulfo-NHS | 6,100 RU | 38 RU | 93% |

Similarly to Example 5, the improvement caused by the modification with β-alanine was apparent. Not only that the ligand density was enhanced significantly, but also the ligand activity became higher. The improvement in ligand activity is observed in this case even when NHS was used for activation, but even more upon sulfo-NHS activation.

Thus, here again the assay sensitivity was significantly improved by modification with easily-activated CGs. This example is of special meaning, since measuring protein-small molecules interactions with higher sensitivity is one of the "holly grails" in the field of biosensors. The applicative significance of such improvement is clear, for example in the assays for drug discovery.

Example 7

Charge Minimization

Figure 7:
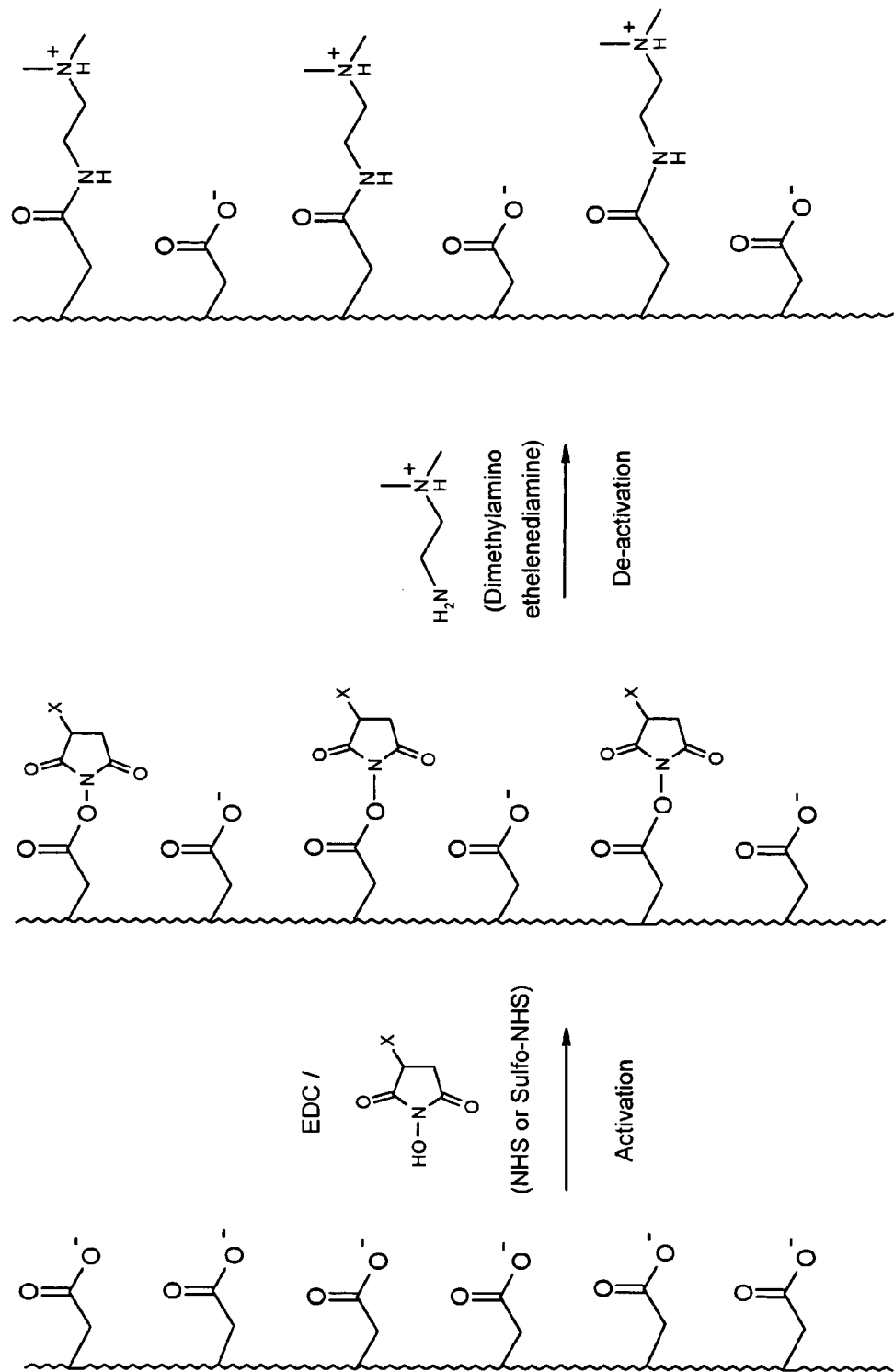
FIG. 7 is a schematic presentation of charge minimization upon activation and following deactivation process with diamine molecules. Note that for achieving non-negative layer after deactivation, at least 50% of the CAs should be activated by NHS (X=H) or sulfo-NHS (X=$SO_3^-$).

Two binding layers based on alginic acid, with or without β-alanine modification, have been compared in similar experiments. The procedure is schematically described in FIG. 7, and the results are summarized in Table 6 bellow.

The sensor chips were activated by exposure to a solution of 0.2 M EDC and 0.05 M NHS or sulfo-NHS (7 min injection), and then immediately deactivated by exposure to 1 M dimethylethylenediamine, pH 8.5 (7 min injection). This process is expected to reduce or even eliminate the negative charge of the layer, since part of the CGs is transformed to positive tertiary amines. More efficient activation will lead to more efficient charge minimization.

The level of negative charge was comparatively estimated by measuring the adsorption of a positive protein, avidin (PI=10.5), to the layer. Avidin (50 ug/ml) was injected for 7 min in 10 mM phosphate buffer, pH 7.4. This test was done prior and after charge minimization.

TABLE 6

Charge minimization in alginic acid layers.

| Layer # | Modification | Activation | Avidin adsorption before charge minimization | Avidin adsorption after charge minimization |
|---|---|---|---|---|
| 2 | None | NHS | 6,000 RU | 5,500 RU |
| 2 | None | Sulfo-NHS | 6,000 RU | 5,500 RU |
| 2E | β-Alanine | NHS | 6,000 RU | 0 RU |
| 2E | β-Alanine | Sulfo-NHS | 6,000 RU | 0 RU |

The results shown in Table 6 provide a clear indication of the outcome of β-alanine modification. While the process of charge minimization had only minor effect on the non-modified layer, the negative charge of the modified layer was totally eliminated. Therefore, it can be concluded that the modified layer was activated more effectively, and thus more CAs reacted with the diamine molecules.

Furthermore, since at pH 7.4 CGs are essentially negative and tertiary amines are essentially positive, it means that at least 50% of the easily-activated CGs were activated by the EDC/NHS or EDC/sulfo-NHS solution. For comparison, it was reported that under similar conditions, only 30-40% of the CGs in a CMD layer were activated (*Anal. Biochem.* 1991, 198, 268-277).

This feature of the layers of the invention has an applicative significance. The process of charge minimization as demonstrated above can be a part of ligand immobilization, in which the ligand is bound after activation and before deactivation. Alternatively, this process can be done either before or after regular ligand immobilization process. In any case, the outcome can be a layer without negative charge after ligand binding. As mentioned above, layers without electrostatic charge at the analyte interaction stage are beneficial for prevention of non-specific binding and other charge interruptions, especially when highly-charged analytes are used.

Therefore, this example represents not only indication for the features of the presented layers, but also a method for achieving effective charge minimization of the layer before, during or after ligand binding. The diamine deactivator has been brought as an example only; similar molecules, e.g ethylenediamine or hydrazine, may be used as well.

The results show no difference between NHS and sulfo-NHS in this case. However, based on other results shown above, it is clear that sulfo-NHS is preferred if the ligand is bound between the activation and deactivation, for achieving more efficient coupling.

The invention claimed is:

1. A binding layer, comprising:
   a polysaccharide substituted by a plurality of carboxylic groups, the plurality of carboxylic groups comprising a plurality of easily-activated carboxylic groups,
   wherein at least one β-atom of each of the easily activated carboxylic groups is a carbon atom and remaining β-atoms are independently hydrogen or carbon atoms,
   the β-carbon atom of each of the easily activated carboxylic groups is linked to a functional group of the polysaccharide through a covalent linkage, the functional group being a native or chemically introduced carboxylic group, or a derivative thereof selected from the group consisting of an ester, an amide, an anhydride, and an acetyl halide,
   wherein at least a part of the plurality of the easily-activated carboxylic groups are activated carboxylic ester groups capable of binding ligand molecules, the activated carboxylic ester groups being obtained by activation of the carboxylic groups of the easily activated carboxylic groups and being selected from the group consisting of a N-hydroxysuccinimide ester and a N-hydroxysulfosuccinimide ester, and the β-carbon atom of the easily-activated carboxylic groups has no electron withdrawing groups.

2. The binding layer according to claim 1, wherein the polysaccharide is selected from the group consisting of agarose, alginic acid, amylopectin, amylose, carageenan, cellulose, chitin, chitosan, dextran, glycogen, heparan, heparin, hyaluronic acid, pectin, amylase, and starch.

3. The binding layer according to claim 1, wherein the polysaccharide is selected from the group consisting of alginic acid, carboxymethyl dextran, carboxymethyl cellulose, hyaluronic acid, and pectin.

4. The binding layer according to claim 1, wherein the ligand molecules are selected from the group consisting of nucleic acids, peptides, proteins, polypeptides, antigens, polyclonal antibodies, monoclonal antibodies, single chain antibodies, antibody fragments, glycan, small organic molecules, cells, viruses, bacteria, and biological samples.

5. The binding layer according to claim 1, wherein the polysaccharide is immobilized onto a solid substrate having a surface.

6. The binding layer according to claim 5, wherein the solid substrate is a sensing element of a biosensor.

7. The binding layer according to claim 6, wherein the sensing element comprises a material selected from the group consisting of glass, plastic, and free electron metals.

8. The binding layer according to claim 7, wherein the free electron metal is gold.

9. The binding layer according to claim 1, wherein the plurality of carboxylic groups or derivatives thereof is activated.

10. The binding layer according to claim 1, wherein at least 50% of the plurality of the carboxylic groups or derivatives thereof is activated.

11. A method for preparing a binding layer comprising a polysaccharide substituted by a plurality of carboxylic groups, the plurality of carboxylic groups comprising a plurality of easily-activated carboxylic groups, each of the plurality of the easily-activated carboxylic groups having at least one β-atom being a carbon atom and remaining β-atoms are independently hydrogen or carbon atoms, the method comprising:

providing a substrate having a surface;
immobilizing a polysaccharide on the surface of the substrate wherein said polysaccharide immobilized on the substrate contains functional groups capable of chemical modification,
chemically modifying the polysaccharide by attaching a plurality of the easily-activated carboxylic groups to extend therefrom, wherein at least one β-atom of each group of the easily-activated carboxylic group is a carbon atom and remaining β-atoms are independently hydrogen or carbon atoms, wherein said attaching comprises linking the β-carbon atom of the plurality of the easily activated functional group to the functional groups of the polysaccharide through a covalent linkage, the functional groups being a native or chemically introduced carboxylic groups, or a derivative thereof selected from the group consisting of an ester, an amide, an anhydride, and an acetyl halide; and
esterifying at least part of the easily activated carboxylic groups for binding of ligand molecules with at least one ester selected from the group consisting of a N-hydroxysuccinimide ester and a N-hydroxysulfosuccinimide ester,
wherein chemically modifying and esterifying may occur, independently of each other, either before, during or after immobilizing, and a β-atom of the easily-activated carboxylic groups has no electron withdrawing groups.

12. The method according to claim 11, wherein the polysaccharide is selected from the group consisting of alginic acid, carboxymethyl dextran, carboxymethyl cellulose, hyaluronic acid, and pectin.

13. The method according to claim 11, wherein at least 50% of the easily activated carboxylic groups or derivatives thereof are esterified to form a plurality of ester groups selected from N-hydroxysuccinimide or N-hydroxysulfosuccinimide esters.

14. The method according to claim 13, wherein the plurality of ester groups are reacted with ligand molecules, thereby affording ligand molecules covalently bound to the layer.

15. The binding layer of claim 1, wherein the polysaccharide is immobilized onto a solid sensing element of a biosensor.

16. The binding layer of claim 15, wherein the polysaccharide is selected from the group consisting of alginic acid, amylopectin, amylose, carageenan, chitin, chitosan, glycogen, heparan, heparin, hyaluronic acid, pectin, amylase, starch, carboxymethyl dextran, and carboxymethyl cellulose.

* * * * *